US005769811A

United States Patent [19]
Stacey et al.

[11] Patent Number: 5,769,811
[45] Date of Patent: Jun. 23, 1998

[54] BLOOD-PROCESSING MACHINE SYSTEM

[75] Inventors: Gary Stacey, Marshfield; Frederick York, Arlington; David Lamborghini, Mansfield; Steven Liberatore, Taunton, all of Mass.

[73] Assignee: Haemonetics Corporation, Braintree, Mass.

[21] Appl. No.: 551,150

[22] Filed: Oct. 31, 1995

[51] Int. Cl.[6] .................................................. A61M 35/00
[52] U.S. Cl. ............................................... 604/4; 604/407
[58] Field of Search ................................... 604/4–6, 407, 604/408–410, 30, 31, 65, 67

[56] References Cited

U.S. PATENT DOCUMENTS

| 4,610,781 | 9/1986 | Bilstad et al. ............................ 210/85 |
| 5,460,490 | 10/1995 | Carr et al. ................................ 417/44.2 |

FOREIGN PATENT DOCUMENTS

| 0384155 | 8/1990 | European Pat. Off. . |
| 0623357 | 11/1994 | European Pat. Off. . |
| WO 80/02376 | 11/1980 | WIPO . |
| WO 94/10921 | 5/1994 | WIPO . |

*Primary Examiner*—John G. Weiss
*Assistant Examiner*—K. Yong O
*Attorney, Agent, or Firm*—Cesari and McKenna, LLP

[57] ABSTRACT

A multiprotocol blood-processing machine and disposable units for use therewith. The disposable units generally comprise a centrifuge bowl for separating whole blood into blood constituents, an inlet tube for conveying blood into the bowl, an outlet tube for conveying the blood constituents away from the bowl, and a manifold for placing the inlet tube and the outlet tube in fluid communication with a tube from a donor. The manifold has a machine-readable barcode label for identifying to the blood processing machine which type of disposable unit is being coupled to it. The machine itself comprises a central processing unit that controls overall operation, a first computer memory containing safety-monitoring instructions that cause the central processing unit to monitor various state parameters in order to ensure donor safety, and a second computer memory containing instructions that define at least one apheresis or blood-processing protocol. In some implementations, the second computer memory is removable from and insertable into the blood processing machine by an operator.

6 Claims, 14 Drawing Sheets

BLOOD-PROCESSING MACHINE SYSTEM

FIELD OF THE INVENTION

This invention relates to blood apheresis, and in particular to automated apparatus for collecting and fractionating blood into components according to defined protocols.

BACKGROUND OF THE INVENTION

Whole human blood includes predominantly three types of specialized cells: red blood cells, white blood cells, and platelets. These cells are suspended in a complex aqueous solution of proteins and other chemicals called plasma. Although in the past blood transfusions have used whole blood, the trend is to transfuse only those blood components required by a particular patient. This approach preserves the available blood supply and in many cases is better for the patient (e.g., by preventing exposure to inadequately or improperly screened blood that may harbor disease).

The blood components needed for the transfusion are taken from a donor by a process called apheresis in which the desired one, or more, specific components of the whole blood are separated and harvested by a blood-processing machine. The remaining components are then returned to the donor.

An overriding concern in the manufacture and use of the blood processing systems is donor safety. To guarantee this safety a number of potential threats to the donor must be continuously monitored by redundant systems. For example, the existence of air in the blood components returning back to the patient, excessive pressure in the returning blood components, the ratio of blood to added anticoagulant, and extracorporeal blood volume are detected by sensors, the outputs of which are continually monitored. Extreme measures in both design and construction of automated blood-processing equipment are taken to avoid malfunction so that any possible danger to the patient or donor is negated. For example, present-day equipment ordinarily includes systems for monitoring operating voltage, centrifuge spin rates and continuous data-processing operation.

Current blood-processing systems typically consist of two main components. A disposable, i.e., one-time-use product (or product set) that is used for a specific purpose then discarded; and a multipurpose blood processing machine unit that performs various functions in connection with various protocols. See, for example, U.S. Pat. No. 5,387,187 (issued Feb. 7, 1995), herein incorporated by reference in its entirety. Two exemplary protocols that lend themselves to automation are the "single-donor platelets" (SDP) protocol and the "platelets and plasma" (PLP) protocol; both of these protocols can be carried out with the same disposable set. In the SDP protocol, a platelet concentrate is collected from an individual donor in one procedure. Blood is drawn from the donor and passed through a centrifuge bowl, which separates the blood into red cell, white cell, platelet and plasma components. The platelet fraction is collected, ordinarily in a removable, sterile blood bag, until a desired yield is obtained; the remaining fractions are returned to the donor. In the PLP protocol, both platelet and plasma fractions are retained, ordinarily in separate containers. Specific parameters and operating procedures to effectuate these protocols are well-known to those skilled in the art. Other apheresis protocols (e.g., harvesting of fresh plasma; therapeutic plasma exchange, in which a patient's plasma is replaced with plasma from a healthy donor; mononuclear cell collection, in which white cells are removed; and red-cell collection, in which red cells are removed) are also well-characterized in the art.

The disposables used in these protocols generally consist of a centrifuge bowl and blood-compatible tubing coupling various blood bags and anti-coagulant bags to input/output ports on the bowl. For example, see the disposable apparatus illustrated in FIG. 1 of U.S. Pat. No. 4,946,434, incorporated herein in its entirety by reference. The bowl may be a plastic/transparent centrifuge bowl of the type described in U.S. Pat. No. 5,045,048 (issued Sep. 3, 1991) or U.S. Pat. No. 4,983,158 (issued Jan. 8, 1991), each of which is incorporated herein by reference in its entirety. Usually, the disposable is pre-packaged in a sterilized container for delivery to the end user, who actually installs it on the blood-processing machine. Due to the disassociation between the machine and the protocol, it is of vital importance that only the correct disposables be used with the correct machine protocol and vice-versa.

SUMMARY OF THE INVENTION

Generally, an aspect of present invention is directed to a disposable product. The product includes a manifold which carries a machine-readable indication identifying the type of disposable to a multiprotocol blood-processing machine. An aspect of the invention is also directed to the software architecture by which the information concerning sequence steps of a blood-processing protocol reside in a separate part of machine memory (e.g., a computationally distinct memory partition or a physically distinct memory device, such as a user-insertable memory card), so that it remains discrete from the machine's safety-monitoring software. The disposable may comprise, for example, a centrifuge bowl for separating whole blood into blood constituents, an inlet tube for admitting blood into the bowl, an outlet tube for conveying the separated blood constituents from the bowl, and a manifold for placing the inlet tube in fluid communication with a donor and with the outlet tube via the bowl. As previously indicated, the manifold carries a machine-readable indication identifying the type of disposable to the blood-processing machine.

In preferred embodiments, the machine-readable indication is a bar-code label. Also, the disposable type is identified by the machine-readable code so that the blood processor can ensure that the disposable corresponds to a selected apheresis or blood-processing protocol. The manifold may also comprise arcuate tubes that cooperate with peristaltic pumps of the blood-processing machine.

In general, according to another aspect, the invention features a method in a blood-processing machine for ensuring proper matching between a disposable and a selected apheresis or blood-processing protocol. In accordance with this method, an operator selects one of a plurality of protocols. Then, the type of disposable installed on the blood-processing machine is automatically detected. The detected disposable type is compared with a database of disposable types compatible with the selected protocol, and the blood-processing machine disabled if the disposable does not appear in the database (i.e., is incompatible with the selected protocol). Alternatively, protocol selection is accomplished automatically, as a consequence of installation of a particular disposable; the blood-processing machine electronically senses the type of disposable and selects, on that basis, the appropriate protocol.

In general, according to another aspect, the invention features a multiprotocol blood-processing machine capable of separating whole blood from a donor into isolated blood components and returning some of the blood components back to the donor. This machine includes a central processing unit (CPU) for controlling the blood-processing machine, a first portion of memory containing safety-checking software for enabling the CPU to monitor the machine so as to ensure donor safety, and a second portion of memory containing instructions that direct the CPU to operate the blood-processing machine to perform the protocols. In preferred embodiments, the second portion of memory is removable from and insertable into the blood-processing machine by an operator; however, it can instead be permanently installed within the blood-processing machine. The first and second portions of memory can also reside in the same memory device.

In more specific embodiments, sensors are provided that generate outputs to enable monitoring of donor safety. A hardware safety card associated with the blood-processing machine receives CPU state information and sensor output; based on this information, the safety card continuously determines whether the machine is operating within safe limits.

The first portion of memory may also contain an operating system for controlling the overall operation of the CPU, safety-monitoring software, and software defining an instrument-control manager that implements the sequence steps that define the various protocols, directing the blood-processing machine to perform these sequence steps as appropriate; the sequence steps themselves are preferably stored in, and retrieved by the control manager from, the second portion of memory.

In general, according to another aspect, the invention features a method for restricting selectable protocols in a multiprotocol blood processing machine. This method comprises placing protocol instructions defining a blood processing protocol performable by the blood processing machine onto a memory card insertable into the machine by an operator. Safety-monitoring software, enabling a central processing unit of the blood processing machine to monitor donor safety, resides on a memory device within the blood-processing machine. An operator selects one of the protocols defined on the memory card, after which the machine performs the selected protocol in accordance with the instructions on the memory card. Simultaneously, the safety-monitoring software continuously tracks donor safety.

In specific embodiments, the operator performed steps further comprise illustrating a proper technique for hooking a donor to the blood processing machine, illustrating of the processes performed in a blood processing protocol, and illustrating a proper technique for unhooking the donor from the blood processing machine.

In a related aspect, the invention ensures compatibility between a blood-processing machine and a disposable set installed thereon by electronically identifying the disposable type, then determining whether the identified type is compatible with the machine.

The above and other features of the invention including various novel details of construction and combinations of parts, and other advantages, will now be more particularly described with reference to the accompanying drawings and pointed out in the claims. It will be understood that the particular method and device embodying the invention is shown by way of illustration and not as a limitation of the invention. The principles and features of this invention may be employed and various and numerous embodiments without the departing from the scope of the invention.

BRIEF DESCRIPTION OF THE DRAWINGS

In the accompanying drawings, like reference characters refer to the same parts throughout the different views. The drawings are not necessarily to scale, emphasis instead being placed upon illustrating the principles of the invention. Of the drawings.

DETAILED DESCRIPTION OF THE INVENTION

Figure 1:
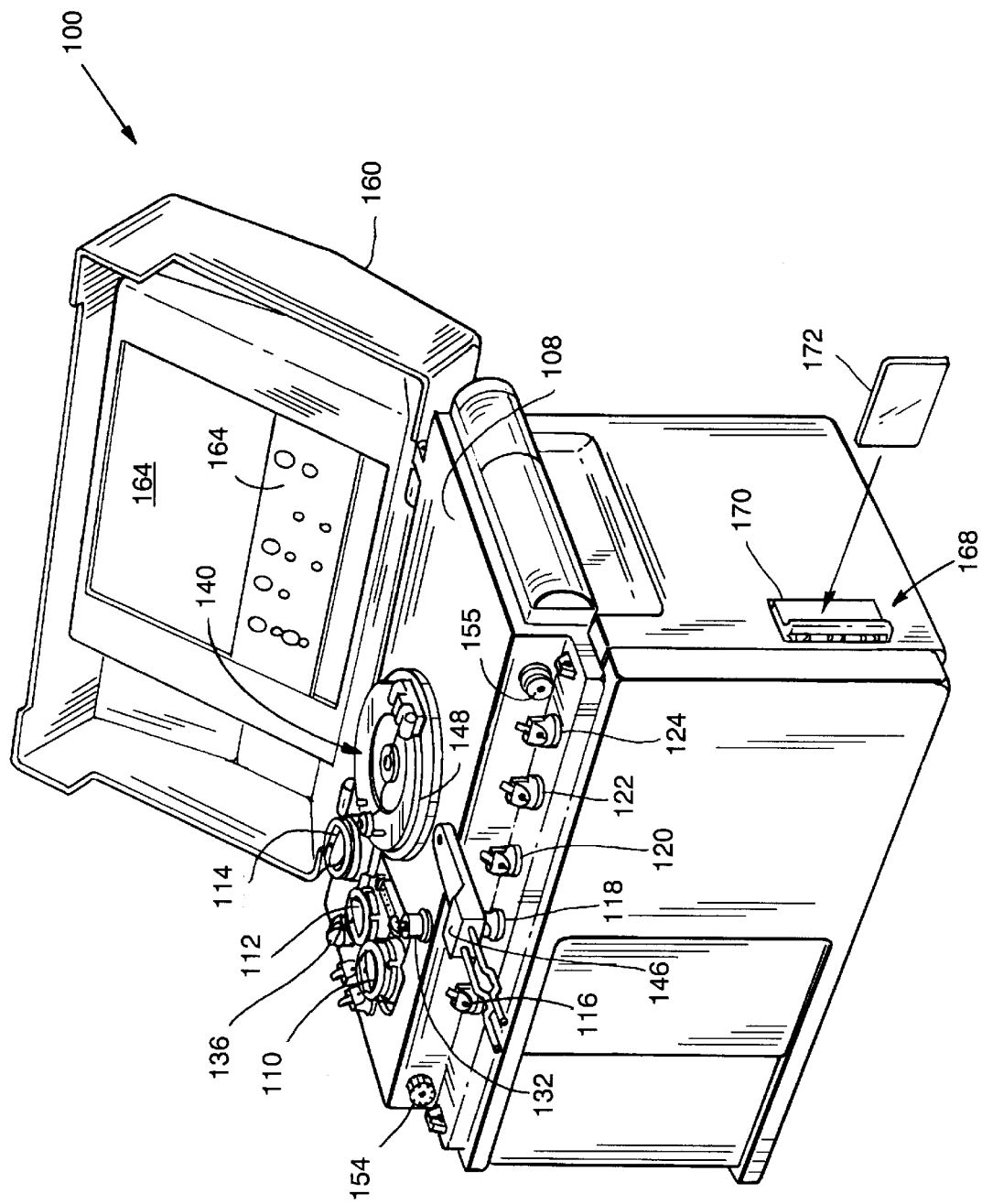
FIG. 1 is a perspective view of the blood-processing machine of the present invention.
Figure 2:
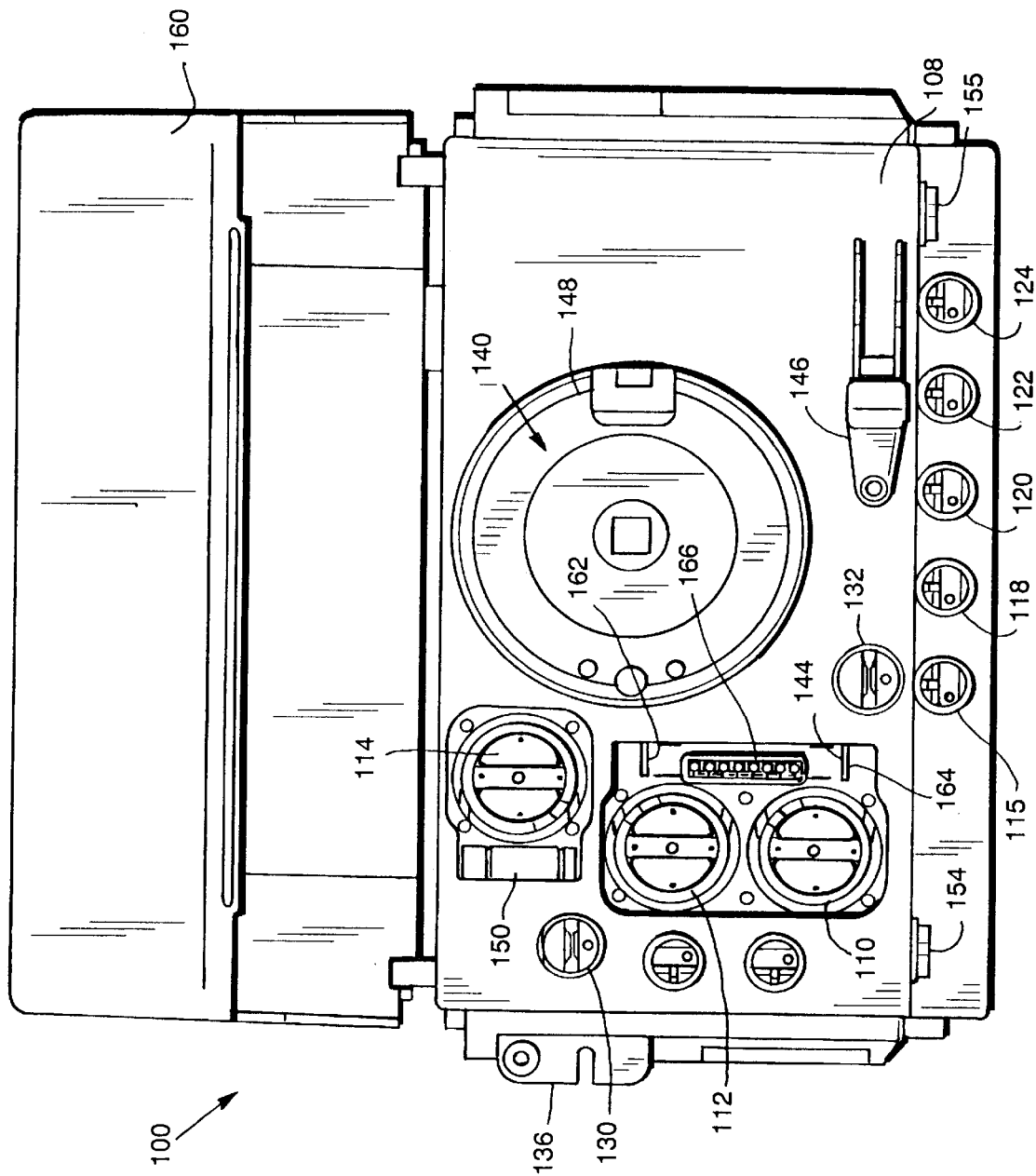
FIG. 2 is a top plan view of the blood-processing machine.
Figure 3:
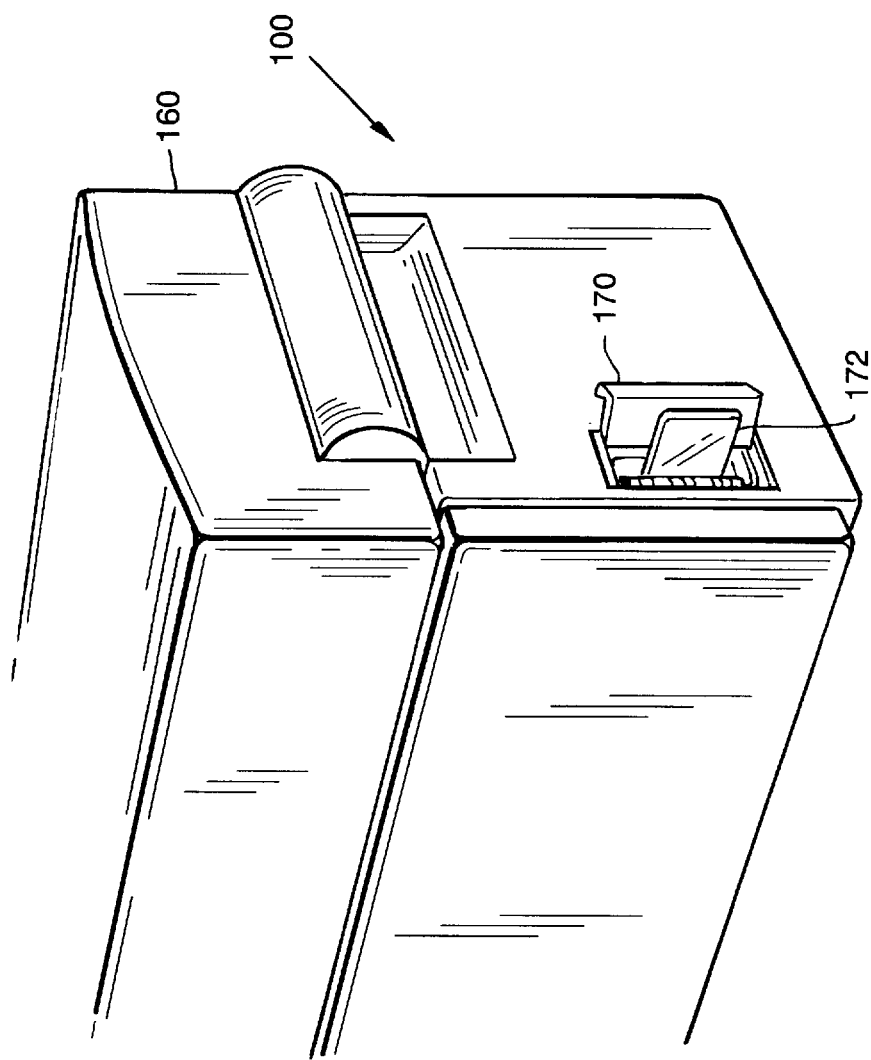
FIG. 3 is a partial side perspective view of the blood-processing machine.

Refer first to FIGS. 1 through 3, which illustrate a multiprotocol blood-processing machine 100 constructed according to the principles of the present invention. Generally, a top panel 108 of the blood-processing machine 100 supports three peristaltic pumps 110, 112, 114; a series of pinch valves 116, 118, 120, 122, 124; a pair of air detectors 130, 132; a drip counter 136; a centrifuge well 140; a donor pressure monitor 154; a system pressure monitor 155; and a weigher 146. These components cooperate with a disposable installed on top panel 108. A lid 160 closes over top panel 108 for storage purposes. A control panel 164 and a display panel 162, provided on an inner side of the lid 160, provide information to and receive commands from an operator when the lid is open and machine 100 in operation.

The specific components of a representative disposable 400 and the components of blood-processing machine 100 with which they cooperate appear in FIG. 4, and are described in greater detail below. With particular reference to FIGS. 1 and 2, the centrifuge well 140 contains a vacuum chuck 140 (not shown) that receives the bowl body of a centrifuge bowl 410. The vacuum chuck holds centrifuge bowl 410 (see FIG. 4) within the well 140, and a cover 148 closes over the well and bowl. Further details of a representative well construction are shown in U.S. Pat. No. 4,889,524 (issued Dec. 26, 1989), incorporated herein in its entirety by reference. The centrifuge well 148 also incorporates bowl optics 142 (not shown in these views) that detect levels of different fluid components within the bowl by sensing the transmissivities of those fluids.

The pinch valves 116, 118, 120, 122, 124 interrupt fluid flow in the tubes of disposables during the course of machine operation. A blood-line air detector 132 and an anticoagulant air detector 130 detect the presence of air in the tubes to the donor and from the anticoagulant source, respectively. A blood pump 110, an optional surge pump 112, and an anticoagulant pump 114 move whole blood, the separated blood constituents, and anticoagulant, respectively, through the tubes between the anticoagulant source, the donor, and the various blood component storage bags described below. An anticoagulant drip counter 136 monitors passage of anticoagulant through an anticoagulant chamber of the disposables. Blood-component storage bags hang from a weigher 146 that monitors the overall quantity of the components removed from the donor. A rigid plastic manifold of the disposables engages a manifold holder 144; similarly, an anticoagulant tube support is detachably held by an anticoagulant pump holder 150. A system pressure monitor 155 and a donor pressure detector 154 detect pressure in the disposable.

The blood-processing machine 100 is preferably capable of performing various apheresis and blood-processing protocols, e.g., the SDP protocol, the PLP protocol, therapeutic plasma exchange, mononuclear cell collection, and red-cell collection. To perform any one of these protocols, the operator chooses and installs a properly configured disposable and also invoke the corresponding protocol-implementing software in the machine. The software controls the operation of the machine, causing it to perform the sequence steps that define the protocol.

Figure 4:
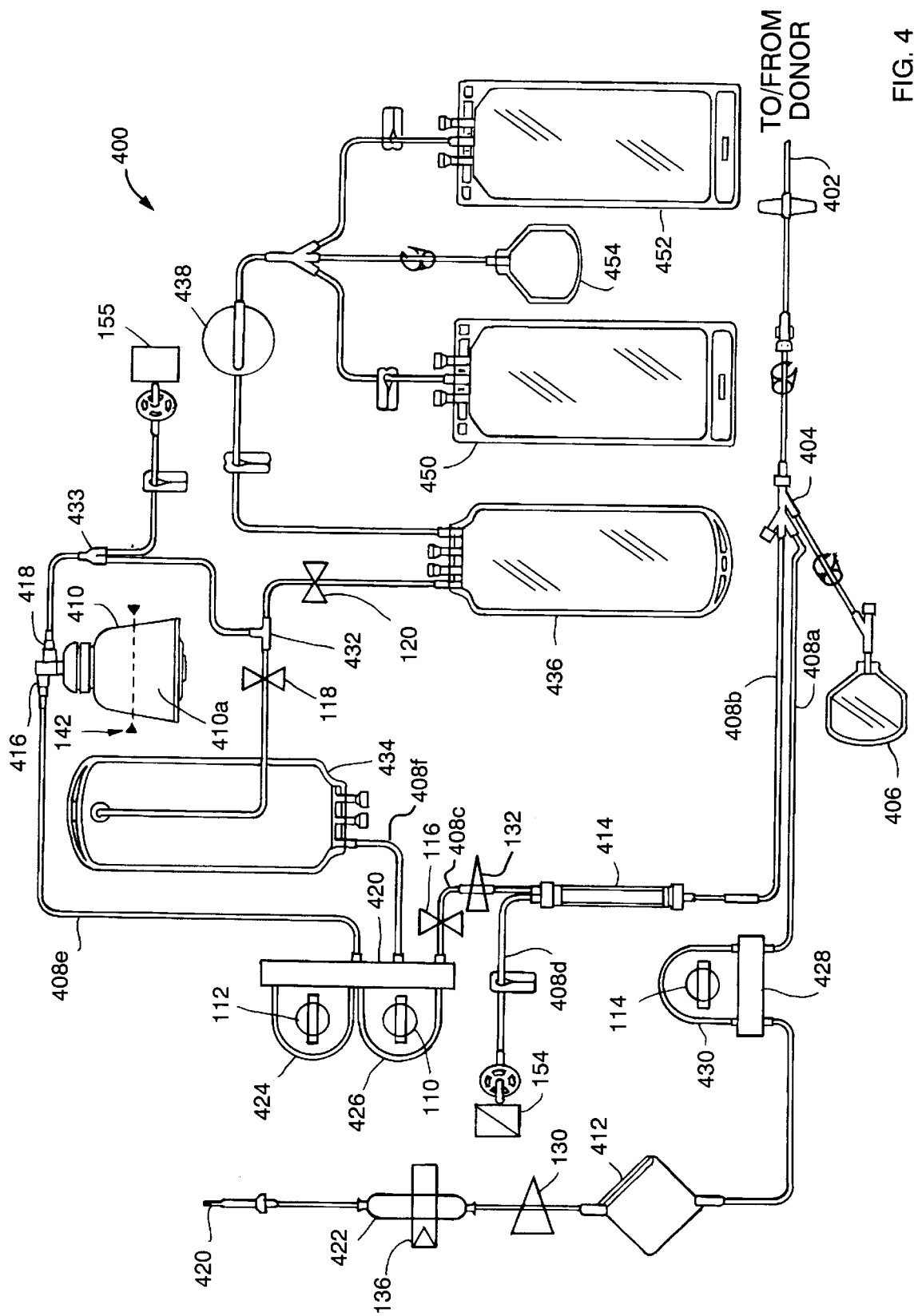
FIG. 4 illustrates an exemplary disposable for the blood-processing machine, schematically showing the points of connection thereto.

FIG. 4 shows an exemplary disposable 400 configured for the SDP protocol. Also schematically shown in FIG. 4 are the components of machine 100 that cooperate with the disposable at various points of connection. It should be noted that differently configured disposables may be required for other ones of the protocols indicated above. These other disposables are also compatible with machine 100, and the invention is not limited to a particular disposable configuration or type of blood-processing machine; accordingly, the machine description supplied herein is intended as exemplary rather than limiting.

Disposable 400 generally comprises a pair of storage bags 450, 452, tubes, and a centrifuge bowl 410, all of which are pre-sterilized. The interior passages of disposable 400 are entirely sealed from the blood processing machine 100 and the outside air to avoid contamination. Basically, blood-processing machine 100 controls the flow of blood and anti-coagulant into and out of the bowl 410 using pumps 110, 112, and 114, and pinch valves 116, 118, 120, and 122. Bowl 410 is a blood separator that utilizes centrifugal forces to fractionate the blood from the donor.

A needle 402 is used to perform the venipuncture of the donor. The needle 402 supplies the blood, via a tube, to a four-port connector 404. Connected to one outlet of this four-port connector is a whole-blood sample bag 406, which admits a sample of the donor's blood for testing. Also connected to the four-port connector 404 is a tube 408a providing anticoagulant, which is drawn from a reservoir (not shown). Downstream of the anticoagulant reservoir is a clear plastic tube 422, which communicates with the drip counter 136 that detects the flow of anticoagulant. A bacterial filter 412 is connected in-line to ensure that bacteria from the donor's blood or bacteria from the anticoagulant source is captured to prevent any cross-contamination of the collected blood. An anticoagulant tube support 428 provides a rigid structure for an arcuate tube 430, which cooperates with the anticoagulant pump 114. Pump 114 precisely controls the flow of anticoagulant into the four-port connector 404. An anticoagulant line air monitor 130 detects any introduction of air from the anticoagulant reservoir.

A tube 408b connects the four-port connector 404 to a blood filter 414 that filters large insoluble material (e.g., clotted blood) from the blood components returned to the donor. Another tube 408c connects the blood filter 414 to a manifold 420. On this length of tubing, a blood line or "red" valve 116 and a blood line air detector 132 are disposed adjacent to the tubing 408c so that fluid flow to the donor can be selectably cut off and any air in tube 408c detected. Also, a tube 408d connects the donor pressure monitor 154 to the return flow to the donor.

Manifold 420 is a blood coupler that connects tubes between ports of the bowl and from/to the donor. It supports two lengths of arcuate tubing 424, 426 which fit over the blood pump 110 and the surge pump 112. Tubing 408e then connects the manifold 420 to an input port 416 of the centrifuge bowl 410. The bowl optics 142 detect fluid levels within the bowl 410. An output port 418 of the bowl 410 connects to a "T" connector 433 that divides fluid from the bowl 410 between an air/plasma bag 434, which connects back to the manifold 420, and a reservoir bag 436. System pressure monitor 155 is connected by T connector 433 to the output port 418 of the centrifuge bowl 410, enabling monitor 155 to detect system pressure at this point.

A second pinch or "yellow" valve 118 is enables shut-off any flow between the "T" connector 432 and the air/plasma bag 434. A green valve 120 enables shut-off of flow between the "T" connector 432 and the reservoir bag 436. Leading out of the reservoir bag 436 is white blood cell filter 438, which filters white blood cells from the platelets to be stored into first and second platelet bags 450, 452. Also connected to the output of the white blood cell filter 438 is a platelet sample pouch 454, which holds a sample of the collected platelets that may be taken during the performance of the protocol.

During performance of the SDP protocol, the blood-processing machine 100 first enters a draw state in which whole blood is withdrawn from the donor's vein. This is accomplished by developing a negative pressure in the lines connected to the patient's vein by operation of the blood pump 110. Simultaneously with the withdrawal of the whole blood, the anticoagulant pump 114 is operated so that anticoagulant is mixed with the blood at the four-port connector 404. The centrifuge bowl 410 is brought up to a predetermined separation speed (approximately 4,800 revolutions per minute typically); yellow valve 118 is opened and green valve 118 closed. The blood pump 110 propels the whole blood, now mixed with anticoagulant, through tube 408e into the input port 416 of the centrifuge bowl 410, displacing sterile air from bowl 410 into the air/plasma bag 434. Eventually the plasma begins to overflow the walls of bowl 410, and is also directed to the air/plasma bag 434. After about a minute, the surge pump 112 is activated, recirculating the plasma held in the air/plasma bag 434 into the centrifuge bowl 410 via tubes 408f, 424 and 408e. After approximately another minute, a reading is taken with the bowl optics 142 to determine the optical density of the blood components in the bowl 410. Subsequently, a dwell state is entered in which pump 112 continually recirculates the plasma at approximately 100 milliliters per minute through the bowl 410 in order to enhance the separation of the cell layers. After the dwell state the surge state begins, during which pump 112 rapidly pumps the plasma from the air/plasma bag 434 into the centrifuge bowl 410. This surge recirculation of plasma continues until the bowl optics 142 detects the presence of platelets. When that occurs, the green valve 120 to the platelet bags 450, 452 is opened and platelets are collected.

Once no further platelets are detected by bowl optics 142, a return state is entered in which uncollected blood components are returned to the donor. Pump 112 pumps all is plasma in the air/plasma bag 434 into the centrifuge bowl 410, and the mixture of red blood cells and plasma now contained in the centrifuge bowl 404 is returned to the donor by reversing the direction of the blood pump 110. During this period, the blood line air detector 132 actively monitors for the existence of any air in the returning mixture of red blood cells and plasma while the donor pressure detector 154 ensures that excessive pressure is not generated. The platelets collected in the first and second platelet bags 450, 452 are then disconnected and properly stored.

In blood-processing machines dedicated to a single protocol, there is a possibility that an operator might select a disposable that is incompatible either because it is made by different manufacturer or because it was made for a different type of machine. Generally this is not a problem, since in such cases the disposable ordinarily will not physically fit within the machine, preventing its operation. Such is not always the case, however, and the disposable-matching feature of the present invention can be implemented on a single-protocol machine as a means of ensuring compatibility between the disposable and the machine. Of course, the danger of improper disposable selection becomes more significant in the case of multiprotocol blood-processing machines, as contemplated herein. A plurality of disposables are designed to be physically compatible with the blood-processing machine, but only one or a subset of which is compatible with a selected protocol. In the past, responsibility for making the correct selection of the disposable for the desired protocol has rested solely with the machine operator.

Figure 5:
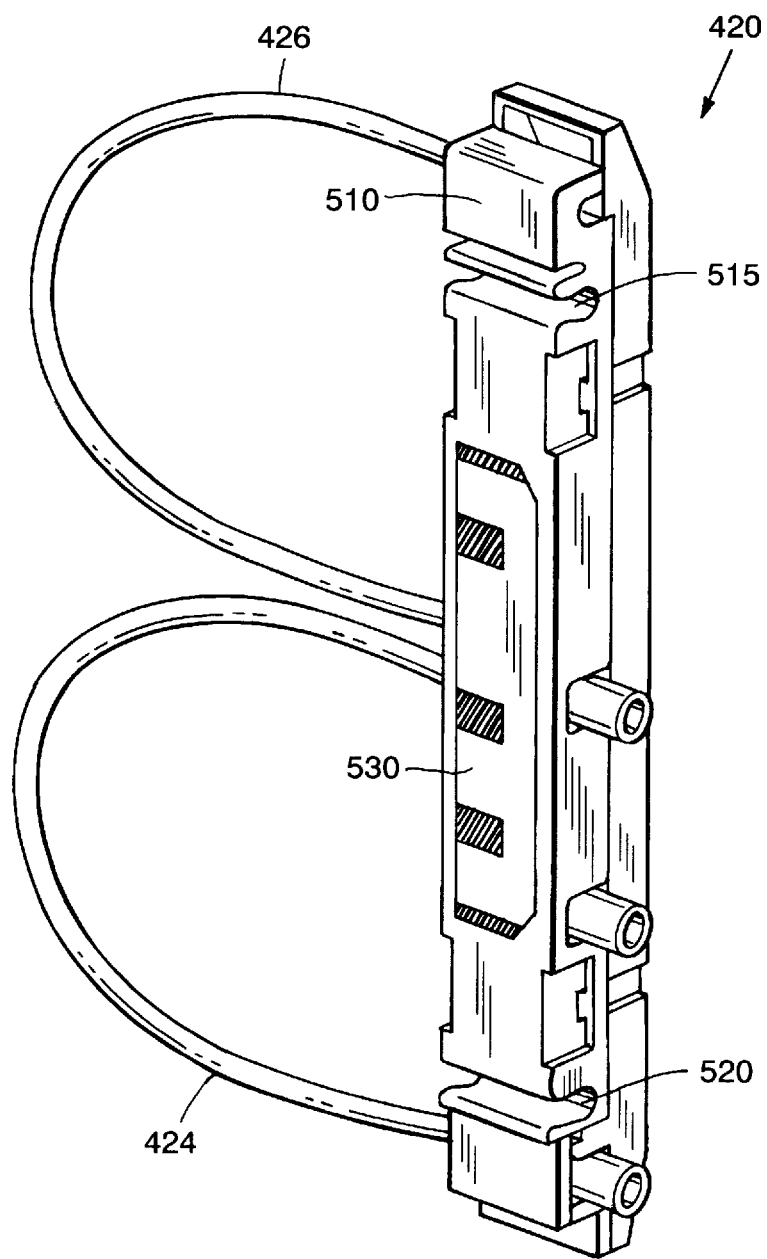
FIG. 5 depicts a manifold for a disposable such as that shown in FIG. 4.

Refer now to FIG. 5, which illustrates an underside of the manifold 420 of the present invention that ensures a proper match between the disposable and the selected protocol. The manifold 420 comprises a rigid plastic housing 510 that supports the two arcuate tubes 424, 426 which cooperate with the pumps 110, 112 to control the passage of fluid in the tubes. Also on a bottom side of manifold 420 are two female clip points 515, 520 formed in the housing 510 and a bar code label 530. The manifold 420 shown in FIGS. 4 and 5 is adapted to be connected into the manifold holder 144 shown in FIGS. 1 and 2 by the engagement of the female clip points 515, 520 over the corresponding male clip points 162, 164. The manifold holder 144 has a light emitter and detector array 166 comprising eight emitter/detector pairs for detecting a bar code imprinted on the label 530. This bar-code label identifies the type of disposable with which it is associated. The array 166 reads this code and conveys the information to appropriate processing components (described below) in the blood-processing machine 100, which verify a proper match between the installed disposable and the particular protocol selected by the operator.

Alternatively, the bar code can be applied to another area of the disposable (e.g., to the origin label on the top side of the manifold) and read by a wand or other manually operated bar-code reading device.

Indeed, the bar code itself, while preferred for its convenience and economy, can be replaced with other forms of electronic tagging. For example, the disposable identity information can be contained on a magnetic strip, or on a low-power broadcast "beacon" detectable by receiving electronics located in the machine 100.

Another safety feature, illustrated in FIG. 3, is the retention of protocol-related information (e.g., the computer code that tells the blood processing machine how to perform particular blood processing protocols) necessary for execution of the protocol in a discrete portion of computer memory, such as on a removable memory card 172. A receiving slot for card 172 is located on one side of machine 100, behind a door 170. Card 172 may also contain security information. In this way, in order to perform a protocol the operator must affix the correct disposable to machine 100 and also insert the proper card into the receiving slot.

This distribution of operating information represents a substantial departure from past practice and confers benefits beyond security. Heretofore, both protocol-dependent instructions (i.e. the information that directs performance of a particular protocol) and safety-related information were not stored discretely from one another, instead residing in an integrated fashion on the same read-only memory (ROM) permanently installed within the machine; as a result, protocol-specific alterations have required reconfiguration, retesting and revalidation of the entire ROM, followed by its replacement by a trained technician. This drawback is particularly acute in actively changing environments, where new protocols are being continually added while older protocols are updated or deleted.

The integrated approach characteristic of prior machines also makes it difficult to selectively accord access not only to the machine but to specific ones of the executable protocols. Although the safety-related information is generally relevant regardless of the particular protocol being performed, the different protocols may not be relevant to the various operators of a given multiprotocol blood processing system. That is, particular operators may need access to only one or two protocols; experimental protocols, for example, should not be available to all operators. Moreover, excessive protocol availability complicates the operator's task since s/he must select from all of the possible protocols a particular machine can perform.

Figure 6:
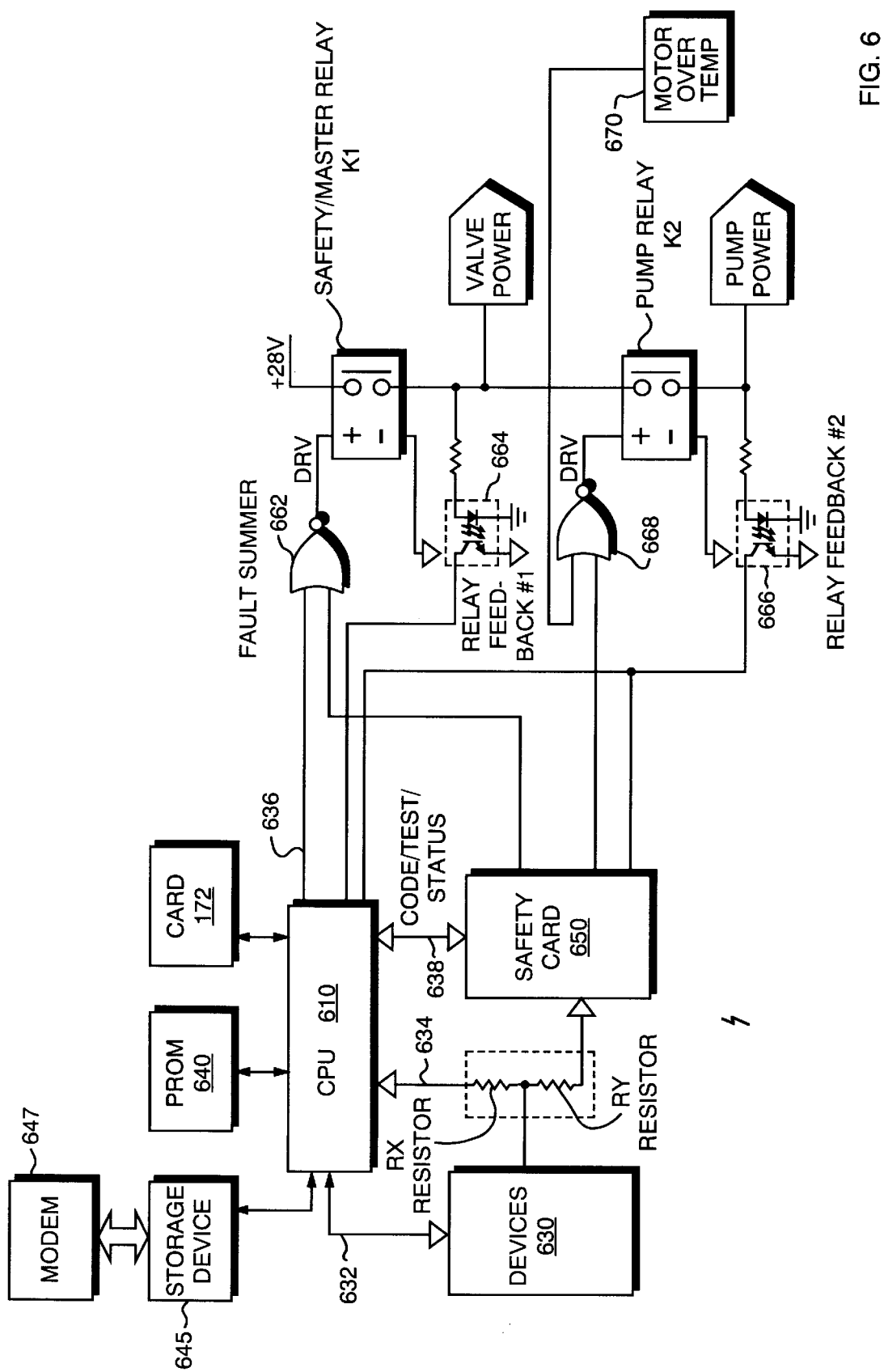
FIG. 6 is a block diagram of the hardware of the blood-processing machine of the present invention.

In one approach, the invention obviates these problems by dividing the code, as shown in FIG. 6, between a PROM 640 and the removable card 172. The PROM 640 contains an operating system and information relating to the monitoring of proper operational thresholds for the maximum allowable air in the tubes, maximum developed pump pressures and speeds, and the maximum amount of whole blood that can be removed from a donor at any given time. In contrast, card 172 contains information particular each protocol for which the machine is adapted. Preferably, card 172 contains sequential instructions that define one or more protocols, and which direct the machine to execute those protocols. Depending on the skills of the operator entrusted with the card, a single or multiple protocols can be contained thereon.

In an alternative approach, the code can be divided between portions of the same memory device by partitioning, i.e., maintaining full functional discreteness between the operating system and the protocol instructions; in this way, protocols can be modified, added or discarded without disruption of the monitoring and safety software. Thus, memory card 172 can contain both the operating system and protocol instructions, or can be dispensed with entirely and all code stored on PROM 640 (or other storage device). As used herein, the term "computationally distinct" refers to maintaining the separation between portions of computer code by physical separation or memory partitioning.

This strategy for code division yields a number of advantages. First, the safety-related code need not be updated and revalidated each time a new protocol is updated or added;

instead, new cards can be created and furnished to end users. Second, the person or entity responsible for proper machine operation can retain control over which operators have access to the machine or can perform particular protocols. By assigning cards for specific protocols only to those operators who have been trained therefor, the risk of improper operation is minimized.

The approach for dividing the software is best be understood with reference to the hardware and software architecture of the blood-processing machine of the present invention. With continued reference to FIG. 6, a CPU 610 controls a series of machine elements or devices 630 of the blood processing machine by signals provided on line 632. "Devices 630" is intended as a generic term covering such operative machine elements as the anticoagulant pump 150, surge pump 112, blood pump 110, the donor and system pressure monitors 154, 155, bowl optics 142, the anticoagulant drip counter 136, the anticoagulant air detector 130, and blood line air detector 132. Operation of CPU 610 is controlled by instructions contained on card 172 and a PROM 640, which in combination define the steps in the protocols and also allow CPU 610 to detect, by monitoring various levels associated with devices 630, unsafe conditions. In particular, CPU 610 monitors the signal outputs from each of these devices, provided on a line 634 through a buffering resistor Rx, and compares these signals with threshold levels specified in PROM 640. In the event that the CPU 610 detects a value mismatch that would threaten the safety of the donor (a "critical fault condition"), the CPU, via line 636, activates or opens the safety/master relay K-1 through the fault summer 662. The opening of relay K-1 interrupts all power to the valves 116–124 and to the pumps 110–114. The CPU 610 senses the state of the relay K-1 through a first relay feedback 664.

In an alternative configuration, machine 100 can be adapted to receive protocols (or changes thereto) by electronic transmission. In this implementation, memory card 172 is replaced with an internal storage device 645, such as a hard disk drive. A communication device 647, such as a modem, receives protocol-related information from an outside source. The operating system executed by CPU 610 is programmed to accept protocols only from legitimate sources, which identify themselves as electronic communication is initiated. In this way, users of machine 100 can immediately obtain the latest available protocols and instructions implementing them, and the manufacturer of machine 100 is spared the inconvenience of direct reprogramming or provision of replacement memory components.

To provide a level of redundancy, a hardware safety card 650 is preferably connected in parallel with the CPU 610, and also monitors the operation of the devices 630. The safety card 650 accepts direct coded information from the CPU 610 concerning the states of the devices 630. In response to this state information, the safety card 650 assesses the operation of devices 630 to ensure that they are operating within safe limits for the particular state. For example, a motor encoder on each of the pumps 110, 112, 114 and signals from the valves 116–122, pressure detectors 154 and 155, and air detectors 130, 132 are sampled to ensure that an unsafe condition does not exist in the context of the particular state. The safety card 650 monitors the same output from the devices 630 as the CPU 610 except that it is buffered by a buffering and isolation resistor RY. The safety card 650 compares the states of the devices 630 to values indicated by a CPU code provided on line 638 from the CPU 610. If the information from the devices 630 agrees with the particular state, then the safety card 650 will not intrude on system operation. If, however, the safety card 650 detects a critical fault condition, it opens the safety/master relay K-1 through the fault summer 662. For example, the following table illustrates representative ranges of operation, for the SDP protocol, of the blood pump 110, anticoagulant pump 114, donor valve 116, donor air detector 132, anticoagulant air detector 130, donor pressure monitor 154, and the quantity of extracorporeal blood volume as determined the weigher 146 for both a draw (in which blood is removed from the donor) and a return (in which the uncollected components are returned back to the donor).

|  | BLD PUMP | | AC PUMP | | DONOR | SENSOR/SAFETY |
|---|---|---|---|---|---|---|
|  | RPM | DIR | RPM | DIR | VALVE | LIMIT SUMMARY |
| DRAW | 20–150 | CW | 1–20 | CW | OPEN | A.C. AIR DET ACTIVE DONOR PRESS. FROM −100 TO +300 mmHg ECV LIMIT = 720 ml |
| RE-TURN | 10–150 | CCW | 0 | — | OPEN | DONOR AIR DET ACTIVE DONOR PRESS. FROM −100 TO +300 mmHg |

The safety card 650 also controls a pump relay K-2 through a fault summer 668. This relay K-2 is opened to remove power to the pumps whenever a critical fault condition is encountered by the safety card 650, when a self-test of the safety card 650 is executed at the beginning of a protocol or in a standby mode, and if a motor over-temperature detector 670 detects overheating of any of the pumps 110–114. A second relay feedback 666 provides an indication of the state of the pump relay K-2 to both the CPU 610 and to the safety card 650. In this way, the safety card 650 independently verifies pump valve and sensor feedback to ensure it is within the safety limits defined by the state information from the CPU 610. If a fault condition is detected, power is shut down from all the valves and safety relevant pumps in addition to generating an audible alarm to warn the operator.

Figure 7A:
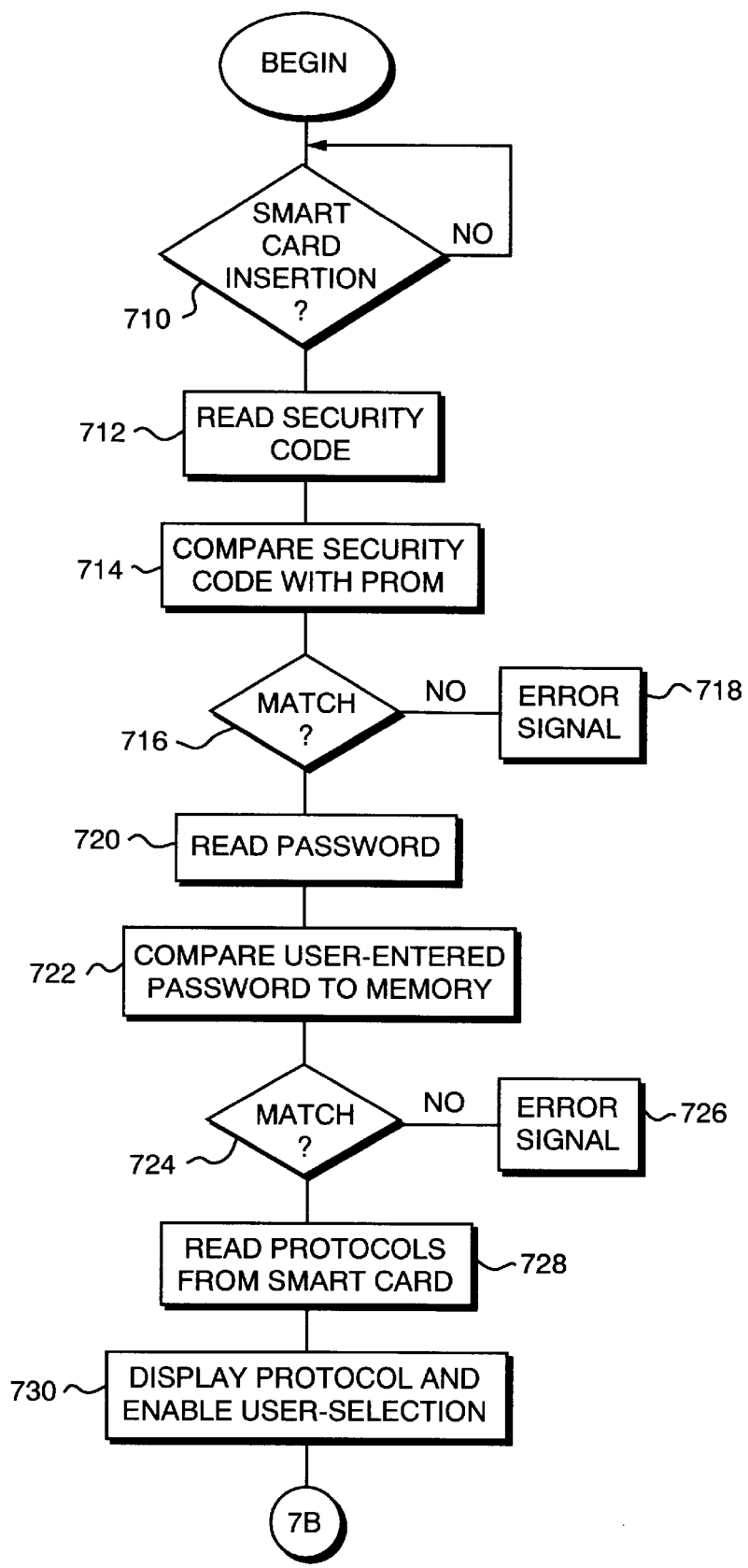
FIGS. 7a and 7b together depict a flow diagram implementing a general process-control architecture.
Figure 7B:
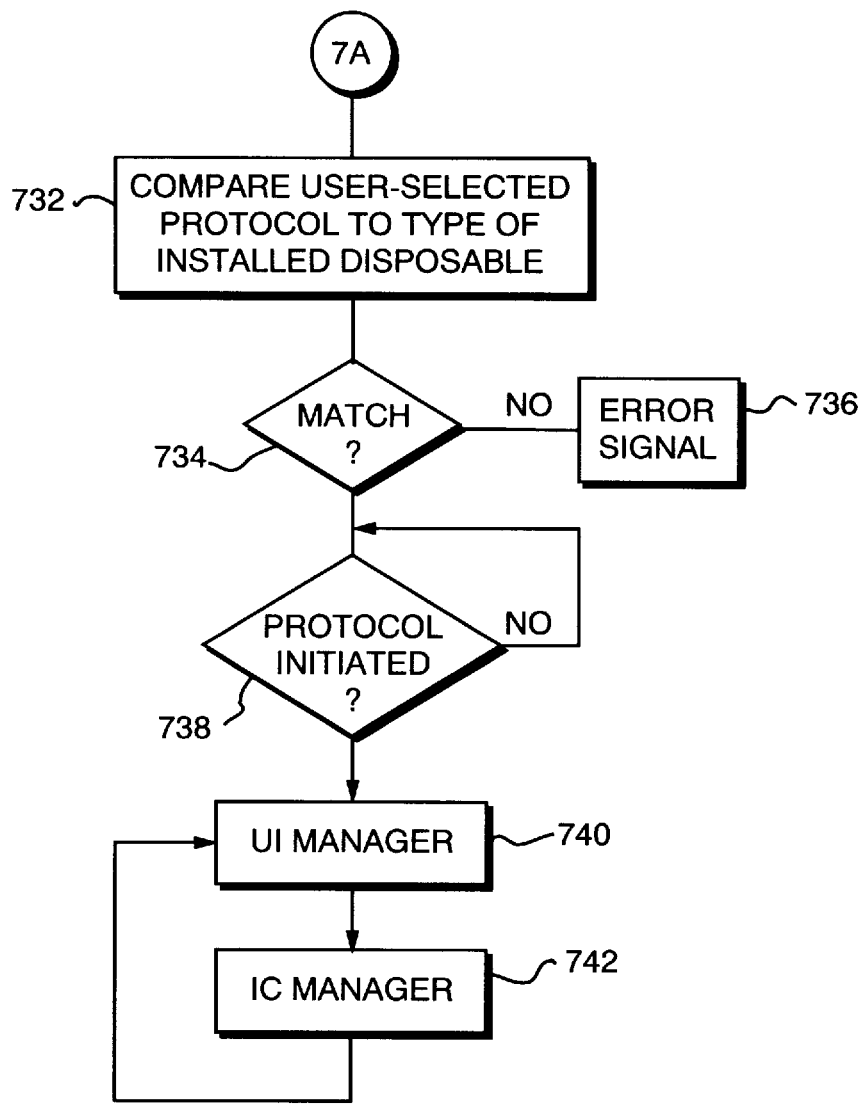

Turning now to a preferred software implementation, at the very highest level a foreground routine called a general process control architecture (GPCA), the operation of which is illustrated in FIGS. 7A and 7B, functions as an operating system to control the execution of various programs including resource allocation scheduling, input/output control, and data management. As illustrated in the figures, the GPCA is designed as a continuous flow system in which two main control units, a User Interface Manager (UIM) 740 and an Instrument Control Manager (ICM) 742 are repeatedly executed after initialization of the system in steps 710–738.

The first step in the initialization process is generally intended to ensure correspondence between the card 172 and the blood-processing machine 100. To accomplish this, insertion of card 172 is detected in step 710, and a security code is read from card 172 in step 712. This security code is compare d with a code stored in the PROM 640. If a proper match is not detected in step 716, an error signal is generated and an alarm sounded in step 718, disabling the machine. At this level, the security code facilitates overall control of access to the machine.

In an optional step 720, the blood-processing machine 100 prompts for and then reads an operator-entered password. This password is compared in step 722 to a password stored on the PROM 640 and/or on the card 172. Again, as determined in step 724, if the operator-entered password fails to match the stored password, an alarm is sounded in step 726 and the machine is disabled. Password entry provides still a further element of access control.

Once the security code on the card 172 and the password have been properly presented to the blood-processing machine 100, the machine reads the protocols stored on the card 178. Then in step 730, these stored protocols are identified to the operator, who may select one of them. The number of protocols selectable by an operator depends on his or her experience. The selected protocol is associated with an identifier corresponding to an allowed type (or types) of disposable; the disposable actually installed on the blood-processing machine is then identified to determine whether it is compatible with the protocol. As described earlier, the blood-processing machine determines the disposable type by reading the bar code label 530 on the disposable manifold 420. In step 734, the blood-processing machine determines whether there is a proper match between the selected protocol and the installed disposable. If not, an error signal is generated in step 736 and the machine is disabled. If a proper match is detected, however, the machine waits in step 738 for the protocol to be initiated by the operator. Once the protocol has been initiated, the user interface manager 740 and the instrument control manager 742 are continually executed.

The GPCA interunit communication method employs message passing between the UIM 740 and the ICM 742. These two modules communicate back and forth to each other by placing messages on each other's queues. The GPCA generally performs the functions of an operating system, i.e., basic hardware control, the execution of application programs and CPU resource scheduling. Although certain tables accessed by the UIM and ICM are contained on the card 172, the GPCA is contained on PROM 640.

Figure 8:
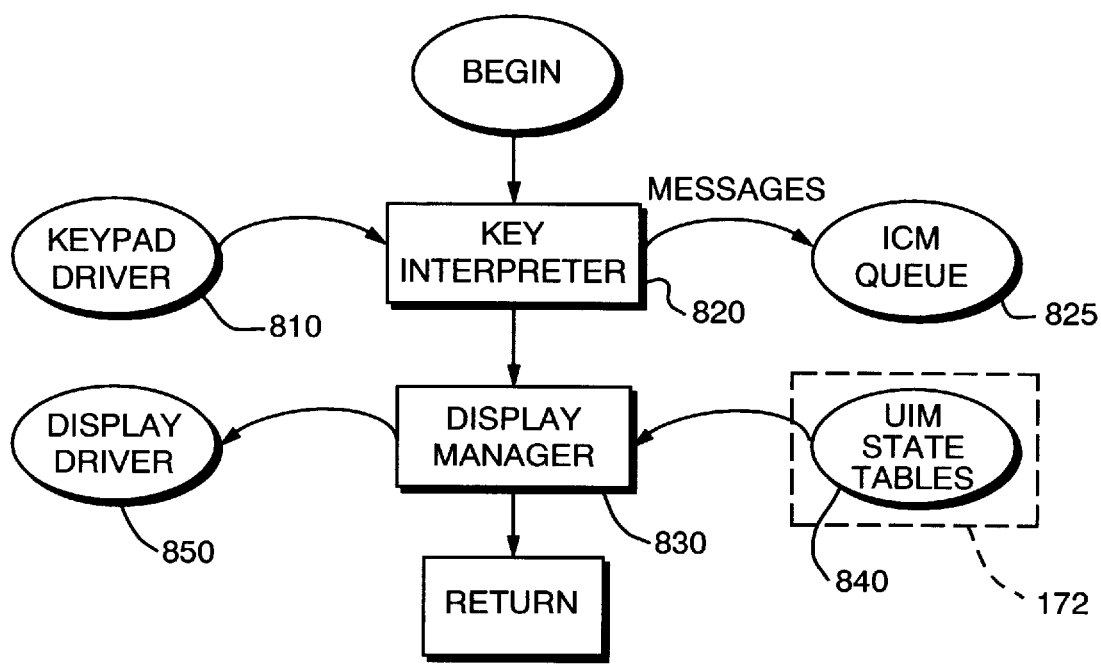
FIG. 8 is a flow diagram implementing a user-interface manager.

As shown in FIG. 8, the UIM 740 performs two main tasks each time it is called by the GPCA. These tasks generally involve communication with an operator. First, the UIM 740 contains a keypad driver 810 that enables a key interpreter 820 of the UIM to monitor the key panel 164 (see FIG. 1) for any operator inputs. Incoming messages from an operator are then passed to the ICM queue 825. The software for controlling key panel and queuing of messages is well-characterized and straightforwardly implemented by those skilled in the art; preferably, this software is located on the PROM 640.

The other operation performed by the UIM is control of the display panel 162. Generally, a display manager 830 of the UIM is responsible for updating the display panel 162 in response to, for example, a state change at the ICM level. Although software that controls the driving of the display 850 is preferably located on the PROM 640, the particular information to be displayed (such the font format and the specific text characters) are preferably located in UIM state tables 840 on the card 172. This distribution is preferred because the particular displayed information is generally protocol-dependent while the software for controlling the display panel is not.

The GPCA also implements the ICM 742, which executes the sequence of steps defining a protocol and operates devices 630 in accordance therewith. The basic ICM code is preferably located on the PROM 640, while protocol sequence steps reside on card 172; the ICM is capable of executing any protocol appropriately arranged into such steps. The PROM 640 preferably also contains hardware-specific code, such as the device drivers that control the pumps, valves, centrifuge, and other machine elements; code for interpreting the raw signals from the devices that provide state information (e.g., the speed of centrifuge 140 and the levels recorded by air detectors 130, 132, drip monitor 136, and bowl optics 142); and the safety-monitoring instructions that define unsafe conditions and their responses thereto, all as described hereinabove.

Memory card 172 contains the sequence tables that define the successive states or steps (ordinarily bundled as sequences, as discussed below) of a protocol and the conditions that determine when each new step is executed. Dynamic linking between the PROM 640 and the card 172 allow their respective software code to remain physically separate while cooperating fully.

Figure 9:
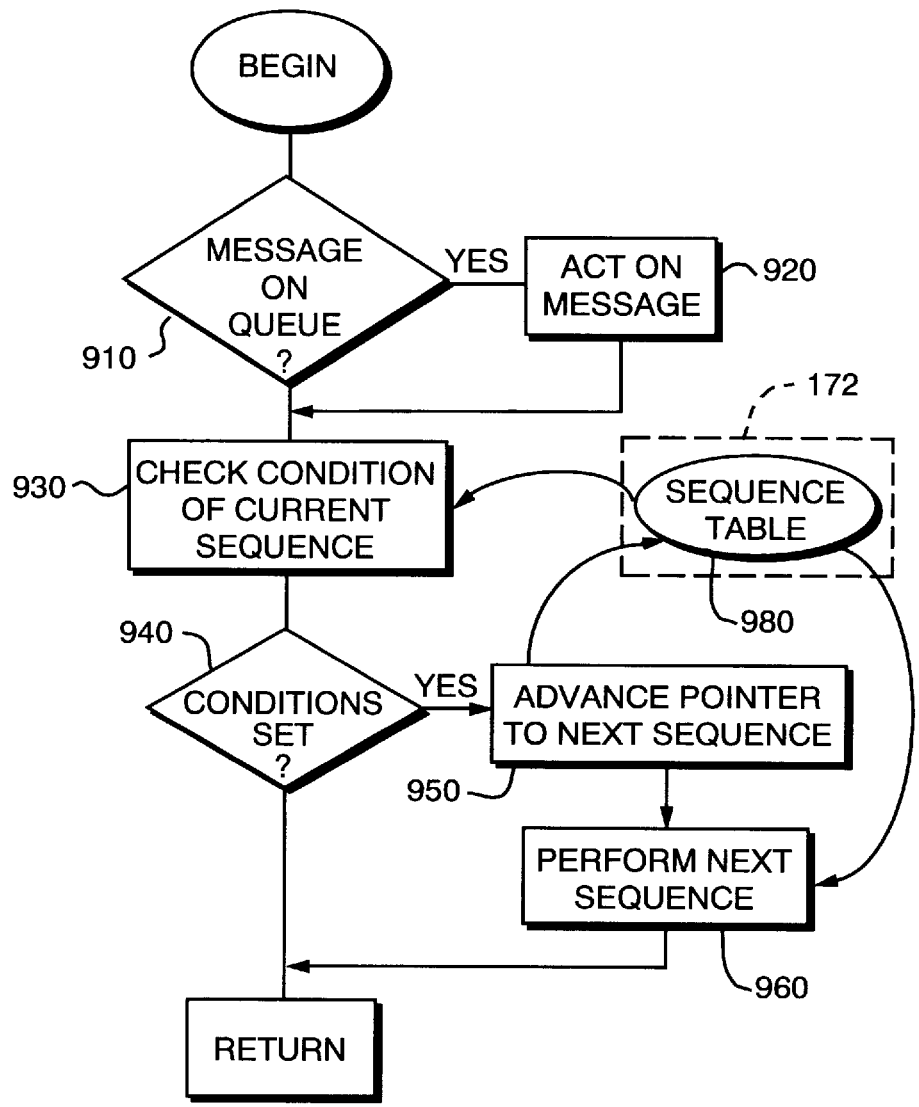
FIG. 9 is a flow diagram implementing an instrument-control manager.

FIG. 9 shows the process steps of the ICM that are performed each time the ICM is called by the GPCA. First, in steps 910 and 920 the ICM acts on any messages available from the UIM. Then the conditions of the current sequence are checked in step 930 by reading from the sequence table 980. This operation is accomplished using a sequence table pointer module that addresses the current sequence table 980. If the conditions are satisfied (step 940), the sequence table pointer is advanced in step 950 and the next sequence is retrieved and executed from the table of card 172 in step 960.

Figure 10:
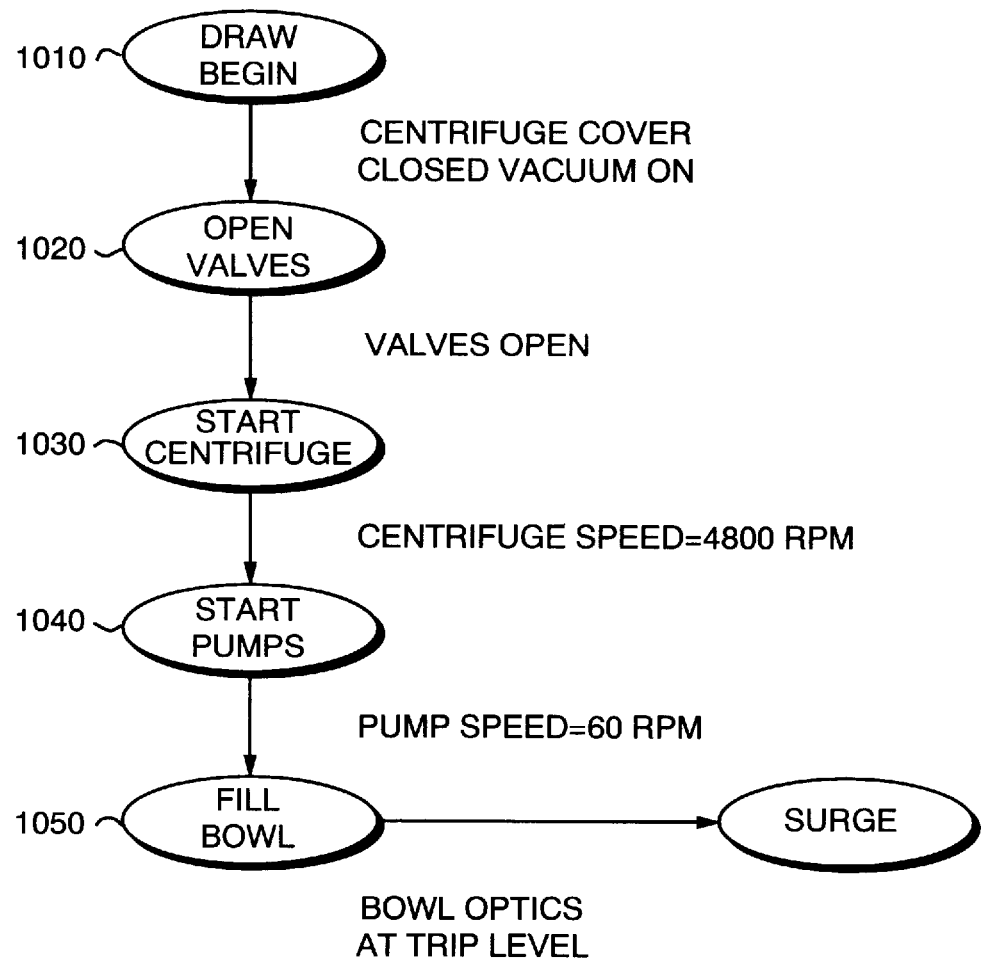
FIG. 10 is a flow diagram of the sequence steps in a draw.

FIG. 10 illustrates the sequence steps that are executed by the ICM for a draw operation, in which whole blood is removed from the donor and pumped into the centrifuge bowl 410; these steps together define the draw operation within the protocol, which itself consists of a plurality of such operations. Upon receipt of the message from the UIM that a draw key has been selected, a sequence table stored on card 172 that defines the steps in a draw operation is accessed by the sequence table pointer.

Figure 12:
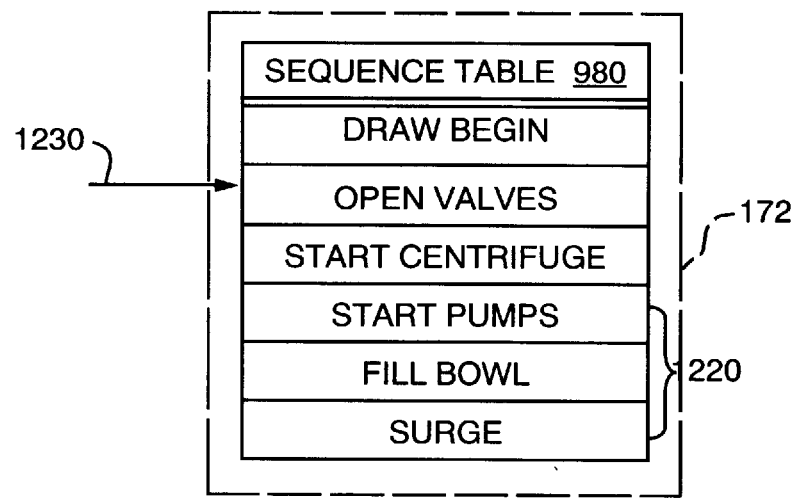
FIG. 12 schematically illustrates a sequence table stored on an insertable memory card.

As shown in FIG. 12, the sequence table 980 in the card 172 sets forth the successive sequences 1220 (each comprising a plurality of steps) representing a protocol. These sequences 1220 are accessed by the sequence table pointer 1230, which is incremented through the table 1210 to next sequence at the completion of the preceding sequence. The first sequence is Draw Begin (shown at reference numeral 1010 of FIG. 10). The conditions indicating completion of this sequence are a closed centrifuge cover and activation of the vacuum chuck holding the centrifuge bowl 410. Once these conditions have been met (as would be determined in step 930 and 940 of FIG. 9), the sequence table pointer 1230 is advanced in step 950 and the next sequence is retrieved in step 960. That sequence involves opening the blood line "red" valve 116 (step 1020 in FIG. 10). The condition representing completion is verification that the blood line valve 116 did in fact open. Execution proceeds to activation of the centrifuge 140 (step 1030 in FIG. 10). After the centrifuge 140 reaches or exceeds a speed of 4,800 rpm, the blood pump 110 is started (step 1040 in FIG. 10). When the pump reaches a speed of 60 rpm,, the bowl 410 begins to fill (step 1050 in FIG. 10). A surge sequence (step 1060 in FIG. 10) is initiated only when the optics 142 of the well 140 have reached a trip level indicating that an adequate amount of blood is now contained in the bowl 410.

Figure 11:
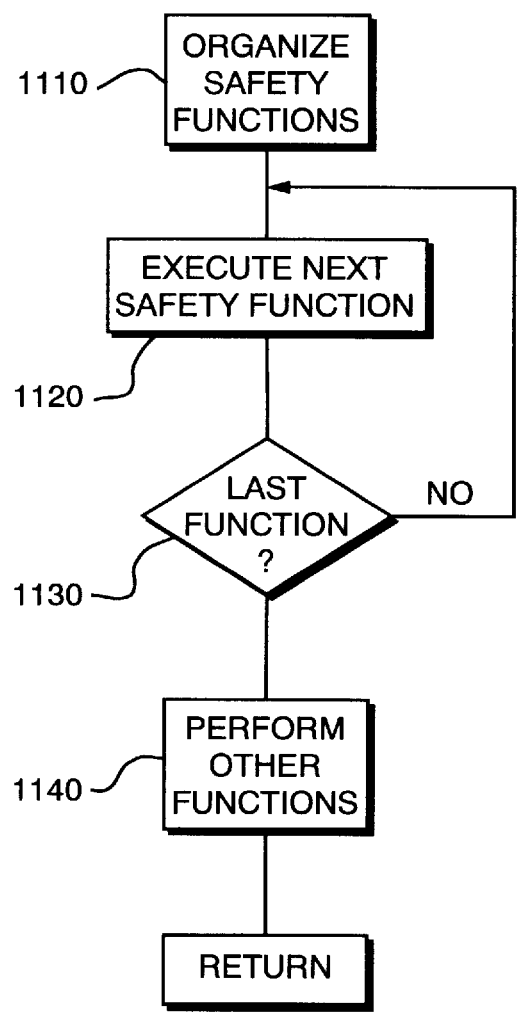
FIG. 11 is a flow diagram of a task manager.

The sequence steps 1220 defined in the sequence table 1210, stored on card 172 and executed by the ICM, do not includes steps to monitor the current state of the blood-processing machine 100 to ensure that no danger exists to the donor. That function is performed by a task dispatcher, whose operation is illustrated in FIG. 11. The task dispatcher is called every 50 ms by an interrupt, and resides on the PROM 640. Every time the task manager is called (i.e., every 50 ms interrupt), safety-monitoring functions are organized in a stack 1110. Then in steps 1120 and 1130, the task manager increments through the stack and performs each of the functions. Finally, in step 1140, other housekeeping functions also assigned to the task manager are performed.

The safety-monitoring functions are generally concerned with reviewing levels associated with the various devices to ensure that the donor is not in any danger. For example, the following tasks are performed every time the task manager is called while a protocol is being performed: pump speed and position monitor task, which ensures that the pumps are operating within safe limits; centrifuge 140 speed monitor task to ensure that the centrifuge's speed is with safe limits; pressure monitor task to ensure that the pressure in the tubes to the donor is not dangerously high or low based on the signal from monitor 154; air detector monitor task to detect air in the tubes to the donor or from the anticoagulant bag based on signals from air detectors 130, 132; and a spill detect task to detect any blood accumulating in the centrifuge well 140.

In summary, the above-described software architecture allows a generic operating system and safety-monitoring system to execute any of a variety of apheresis or blood-processing protocols. Instruction steps defining these protocols may be carried on a operator-insertable card, which can also include password and access-control information.

Figure 13:
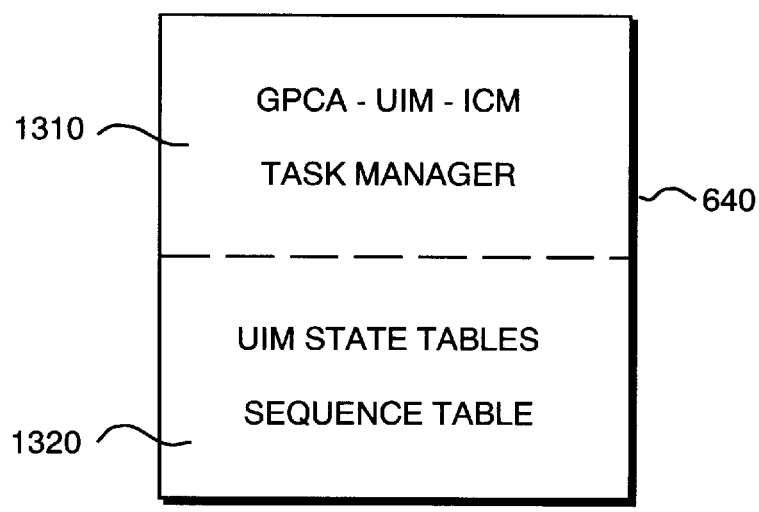
FIG. 13 illustrates the division of code if only a single, internal (i.e., non-insertable) memory device is employed.

In an alternative embodiment, the above-described software architecture can be altered by placing information contained in the card 172 into a separate memory device installed within the blood processing machine or into a discrete portion of the memory on the PROM 640. Specifically, as shown in FIG. 13, the code for the GPCA, UIM, ICM, and task manager may be placed in a portion 1310 of the PROM 640 which is separate from a portion 1320 dedicated to the UIM state tables and sequence tables. Of course, in this embodiment the card 172 is not strictly necessary, sacrificing the advantages associated with provided operator-held "keys" but retaining the ability to separately validate protocol-specific code.

Figure 14:
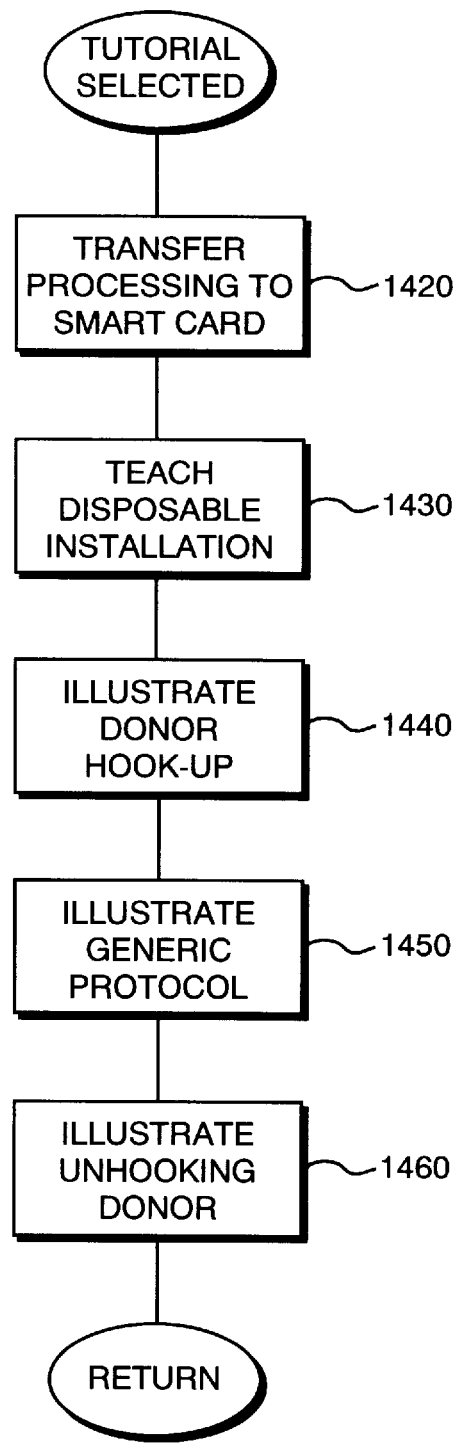
FIG. 14 is a flow diagram of a tutorial selectable from a list of protocols.

In another alternative embodiment, one of the displayed and selectable protocols in step 730 of FIG. 7a can be a tutorial. As shown in FIG. 14, if this tutorial is selected, the processing is transferred entirely to the card 172 in step 1420. As a first part of the tutorial, images stored on the card 172 are successively presented on the display panel 162. These images illustrate, for example, the proper technique for installing the disposable in step 1430. The next part of the tutorial might be hooking the donor to the machine, as illustrated in step 1440. After this demonstration, display panel 162 might provide an illustration of the various processes performed in a generic blood-processing protocol while temporarily activating the corresponding parts of the blood-processing machine 100 in step 1450, thereby acquainting the operator with the machine. Finally in step 1460, the proper technique for unhooking the donor might be presented.

While this invention has been particularly shown and described with references to preferred embodiments thereof, it will be understood by those skilled in the art that various changes in form and details may be made therein without departing from the spirit and scope of the invention as defined by the appended claims. For example, the computer memory components described herein may be implemented as random-access memory (RAM), on EPROMs, Flash ROM or other non-volatile memory, or on mass-storage devices (such as floppy disks or CD-ROMs) readable into RAM.

What is claimed is:

1. A blood-processing machine comprising:
   a. means for collecting whole blood from a donor;
   b. processing means for (i) separating the collected whole blood into isolated blood components and (ii) returning at least some of the blood components back to the donor in accordance with steps defining one of a plurality of protocols:
   c. means for accepting a disposable set comprising blood-compatible tubing configured for at least one specific protocol, and a machine-readable indication for identifying the disposable set to the blood-processing machine;
   d. means for reading the machine-readable indication;
   e. means for removably receiving a computer memory device comprising stored instructions defining one of the protocols;
   f. means for implementing the defined protocol according to the stored instructions; and
   g. control means configured to determine compatibility between the disposable set and the defined protocol and, absent said compatibility, to disable the machine.

2. The machine of claim 1 further comprising:
   a. a database comprising a plurality of stored instruction sets, each set directing execution of a specific protocol by the implementing means;
   b. means for selecting an instruction set from the database for execution by the protocol-implementing means.

3. The machine of claim 2 wherein the means for selecting is an operator-responsive means for enabling selection of a protocol.

4. The machine of claim 2 wherein the means for determining compatibility is configured to select the instruction set from the database based on the machine-readable indication.

5. A multiprotocol blood-processing machine comprising:
   a. means for collecting whole blood from a donor:
   b. a central processing unit for controlling the blood-processing machine to (i) separate the collected whole blood into isolated blood components and (ii) return at least some of the blood components back to the donor in accordance with steps defining one of a plurality of protocols:
   c. a plurality of sensors for monitoring a plurality of machine parameters affecting operational safety:
   d. a first computer memory containing stored instructions which, when executed by the central processing unit cause the machine to periodically assess the machine parameters and effect machine disablement if any of the parameters indicate unsafe machine operation: and
   e. a second computer memory, computationally distinct from the first computer memory, containing instructions that correspond to machine functions defining at least one protocol.

6. The machine of claim 5 further comprising means for accepting a disposable set comprising (i) blood-compatible tubing configured for at least one specific protocol, and (ii) a machine-readable indication for identifying the disposable set to the blood-processing machine, the parameters indicating unsafe machine operation depending on the machine-readable indication.

* * * * *